United States Patent
Krespi

[19]

[11] Patent Number: 5,817,073
[45] Date of Patent: Oct. 6, 1998

[54] APPARATUS FOR ADMINISTERING LOCAL ANESTHETICS AND THERAPEUTIC MEDICATIONS DURING ENDOSCOPIC SURGERY

[76] Inventor: Yosef P. Krespi, 425 W. 59th St., Suite 4E, New York, N.Y. 10019

[21] Appl. No.: 464,321

[22] Filed: Jun. 2, 1995

[51] Int. Cl.⁶ .................................................. A61M 5/32
[52] U.S. Cl. ............................. 604/272; 604/1; 604/164; 604/171; 604/267
[58] Field of Search .................................... 604/51, 54, 1, 604/11, 15, 16, 46, 47, 112, 158, 164, 171, 265, 266, 267, 268, 272; 600/157

[56] References Cited

U.S. PATENT DOCUMENTS

| | | | |
|---|---|---|---|
| 3,506,007 | 4/1970 | Henkin | 604/51 |
| 4,791,937 | 12/1988 | Wang. | |
| 4,886,493 | 12/1989 | Yee | 604/54 |
| 5,169,387 | 12/1992 | Kronner | 604/51 |
| 5,295,952 | 3/1994 | Pietrafitta | 604/15 X |
| 5,339,828 | 8/1994 | Keating et al. | 604/1 X |
| 5,514,084 | 5/1996 | Fisher | 604/1 |
| 5,522,795 | 6/1996 | Green et al. | 604/1 |

Primary Examiner—Michael Powell Buiz
Assistant Examiner—N. Kent Gring

[57] ABSTRACT

A method of and apparatus for administering local anesthetics and therapeutic medications during endoscopic surgery. The method of administering the medication includes inserting an endoscope having a hollow channel through a nasal cavity of a patient, inserting a syringe through the hollow channel and into a selected anatomical site, and inserting medicine into the selected anatomical site through the syringe. The apparatus used for administering the medication includes a tip portion, an outer flexible tube and a flexible member disposed at least in part within the flexible tube. The flexible member has a distal end and is connected to the tip portion at the distal end thereof. The flexible member may also be movable in an axial direction relative to the outer flexible tube such that in a first position the tip portion is disposed within the outer flexible tube and in a second position the tip portion is extended out of the outer flexible tube.

13 Claims, 1 Drawing Sheet

APPARATUS FOR ADMINISTERING LOCAL ANESTHETICS AND THERAPEUTIC MEDICATIONS DURING ENDOSCOPIC SURGERY

FIELD OF THE INVENTION

This invention relates generally to endoscopic surgery and more particularly to methods of and apparatus for administering local anesthetics and therapeutic medications during endoscopic surgery.

RELATED APPLICATIONS

This application relates to a similar subject matter as in my U.S. Patent Application for Method and Apparatus for Treating Laryngeal, Esophageal and Bronchial Lesions filed concurrently herewith, the disclosure of which is incorporated herein by reference.

BACKGROUND OF THE INVENTION

Surgery on laryngeal or bronchial lesions, or tumors are presently performed using lasers. This involves administering a general anesthesia and requires a patient to remain in the hospital for a period of time after the operation. If it were possible to administer a local anesthesia, surgery on laryngeal, esophageal and bronchial lesions and tumors could be performed by an in office procedure. Presently, there is no such procedure for administering a local anesthesia for such operations.

Endoscopic needles currently exist such as the one described in U.S. Pat. No. 4,791,937 to Wang; however, they are used together with an endoscope or bronchoscope strictly to obtain biopsy tissue samples.

Thus there exists the need for a method of and apparatus for administering local anesthetics and therapeutic medications during endoscopic or bronchoscopic surgery.

It is accordingly an object of the present invention to provide a method of applying a local anesthetic during surgery on laryngeal, esophageal and bronchial lesions and tumors.

It is another object of the invention to provide an apparatus for applying a local anesthetic during surgery on laryngeal, esophageal and bronchial lesions and tumors.

It is still another object of the present invention to provide a method of and apparatus for administering therapeutic medications to laryngeal, esophageal and bronchial lesions or tumors.

SUMMARY OF THE INVENTION

The foregoing objects are attained by the present invention, which provides a method of and apparatus for administering local anesthetics and therapeutic medications during surgery on laryngeal, esophageal and bronchial lesions and tumors. The invention utilizes a method of and apparatus for administering local anesthetics and therapeutic medications during endoscopic surgery. The method of administering the medication may include inserting an endoscope having a hollow channel through a nasal cavity of a patient, inserting a syringe through the hollow channel and into a selected anatomical site, and inserting medicine into the selected anatomical site through the syringe.

An apparatus which may be used to administer the medication includes a tip portion, a flexible tube and a flexible member disposed at least in part within the flexible tube. The flexible member has a distal end and is connected to the tip portion at the distal end thereof. The flexible member may also be movable in an axial direction relative to the flexible tube such that in a first position the tip portion is disposed within the flexible tube and in a second position the tip portion is extended out of the tube. The tip portion may be a hollow needle, a brush or a piece of gauze or cotton. Further, the flexible member may also be a flexible tube.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a fuller understanding of the nature and objects of the invention, reference should be made to the following detailed description and accompanying drawings, in which.

DESCRIPTION OF ILLUSTRATED EMBODIMENTS

Figure 1:
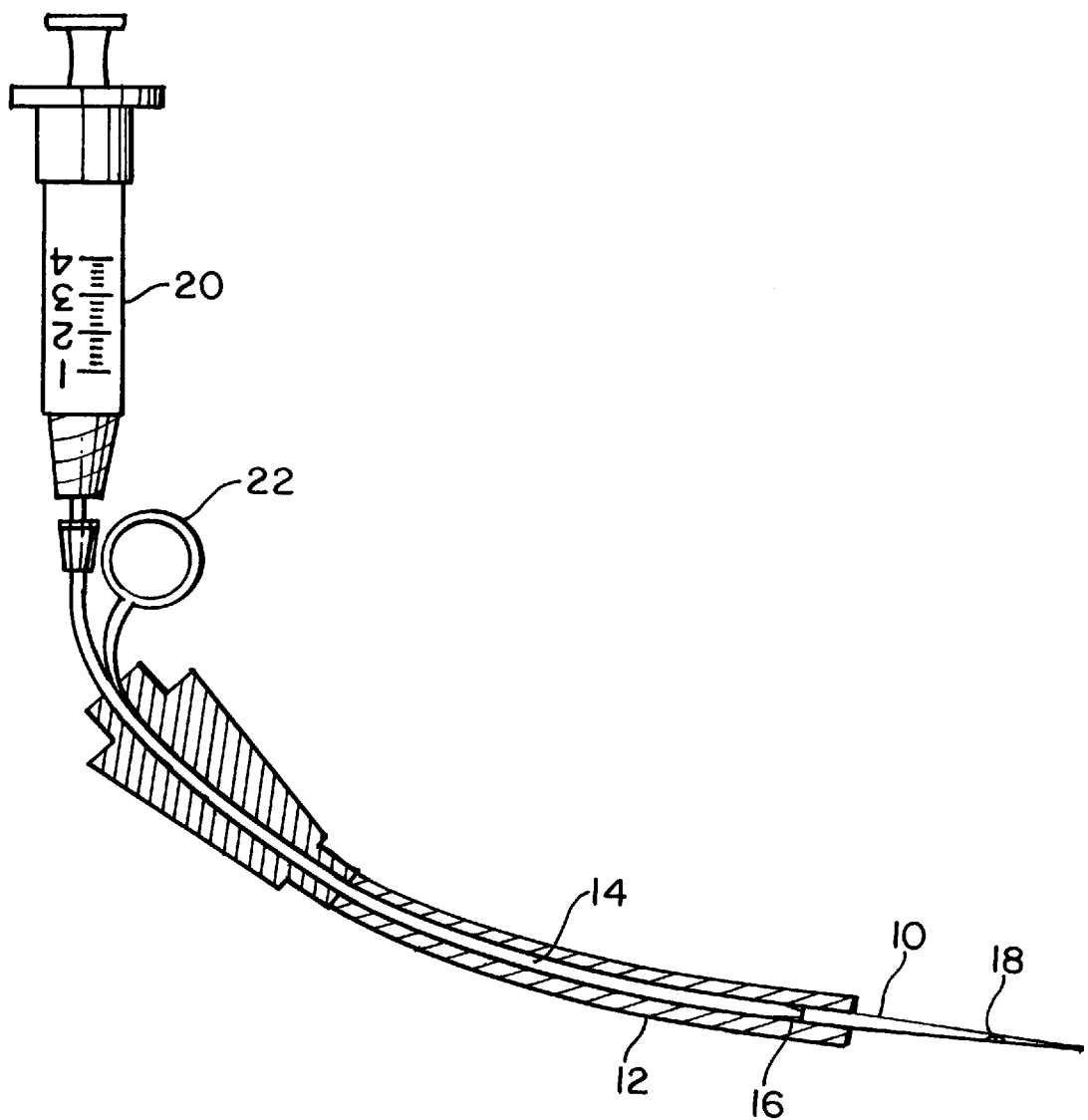
FIG. 1 depicts a cross sectional side view of an apparatus for administering local anesthetics and therapeutic medications during endoscopic surgery in accordance with the present invention.

The present invention involves applying medication such as local anesthetics, steroids, chemotherapeutic agents, and antibiotics and the like to a selected anatomical site during surgery using an endoscope. Generally this includes surgery on laryngeal, esophageal and bronchial lesions and tumors. The surgery includes the use of an endoscope and a flexible instrument that gets passed through an operating channel of the endoscope.

The endoscope used in connection with the present invention is generally known in the art. The instrument that gets passed through the operating channel of the endoscope is illustrated in FIG. 1 and includes a tip portion 10 an outer flexible tube 12, and a flexible member 14 disposed at least in part within the outer flexible tube 12. The tip portion 10 is connected to the flexible member 14 at a distal portion 16 of the flexible member 14. The tip portion 10 may be a hollow needle which has a port 18 to allow fluid to flow through the hollow needle and out the port 18 to a selected anatomical site. The flexible member 14 may be a flexible tube which has a distal end and a proximal end such that the needle 10 is coupled to the flexible tube at the distal end and the two elements are in fluid communication. The instrument may also include a plunger section 20 for inserting a fluid medication into the flexible member 14 through the flexible member 14 through the hollow needle 10 and into the selected anatomical site. Further, the instrument may include a control member 22 connected to the flexible member 14. The control member 22 is for selectively moving the flexible member 14 in an axial direction relative to the outer flexible tube 12 between a first position wherein the tip portion 10 may be located entirely or mostly within the outer flexible tube 12 and a second position wherein the tip portion 10 may be located entirely or mostly extended out of the outer flexible tube 12.

The tip portion 10 may also be a brush for cleaning crust and/or for cleaning laser char and/or for obtaining cytology, or it may be a piece of gauze or cotton for applying medications to the anatomic site.

In one embodiment of the invention, laser surgery is performed as described in my concurrently filed patent application entitled Method and Apparatus for Treating Laryngeal, Esophageal and Bronchial Lesions. The endoscope is inserted into a nasal cavity of the patient, the instrument is inserted through the hollow channel with the tip portion 10 in its first position, the anatomical site is located and the tip portion 10 of the instrument is moved into its second position outside of the outer flexible tube 12. In the embodiment wherein the tip portion 10 is a hollow needle, the hollow needle 10 is inserted into the selected anatomic site, the medication such as a local anesthetic is inserted into the instrument via the plunger portion 20 and into the anatomic site (i.e. a tumor or lesion). Once the medication is inserted into the anatomic site, the needle 10 can be removed from the anatomic site, moved back into its first position and withdrawn from the hollow channel of the endoscope. Once the instrument is withdrawn from the endoscope it may be disposed of.

The instrument is designed for the administration of local anesthetics and therapeutic medications (i.e. steroids, chemotherapeutic agents, antibiotics, etc.) to the organ that is identified for endoscopic laser surgery (i.e. the larynx). In the preferred embodiment the instrument is 2 mm in thickness and is introduced into the operative channel of any flexible fiber optic endoscope for the injection of local anestetic and therapeutic agents. The needle tip 10 can be fully visualized under direct vision through the endoscope and the injection site may be identified in a similar manner. The needle tip 10 may be manipulated with the scope to have 360 degrees of freedom in any direction. The needle may be disposable and accordingly may be discarded under safe conditions like any other contaminated medical device. Further, the instrument may be easily operated by one or two individuals.

It will thus be seen that the invention efficiently attains the objects set forth above, among those made apparent from the preceding description. In particular, the invention provides a method of and apparatus for administering local anesthetics and therapeutic medications during surgery on laryngeal, esophageal and bronchial lesions and tumors. Those skilled in the art will appreciate that the configuration depicted in FIG. 1 is distinguishable over the art in that it is used for different purposes than other endoscopic needles, and it contains tip portions that are not anticipated by the prior art.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

1. An apparatus for use with an endoscope comprising:
   an outer flexible tube;
   a flexible fluid carrying member disposed at least in part within said outer flexible tube, said flexible fluid carrying member having a proximal end and a distal end;
   a tip member in communication with said distal end of said flexible fluid carrying member, said tip member including a brush
   said flexible fluid carrying member being movable relative to said outer flexible tube between a first position where said tip member is disposed within said outer flexible tube and a second position wherein said tip member extends out of said outer flexible tube.

2. The apparatus in accordance with claim 1 further comprising a control member wherein said control member in communication with said flexible fluid carrying member for moving said tip member between said first and second positions.

3. An apparatus for use with an endoscope comprising:
   an outer flexible tube;
   a flexible fluid carrying member disposed at least in part within said outer flexible tube, said flexible fluid carrying member having a proximal end and a distal end;
   a tip member in communication with said distal end of said flexible fluid carrying member, said tip member including gauze;
   said flexible fluid carrying member being movable relative to said outer flexible tube between a first position where said tip member is disposed within said outer flexible tube and a second position where at least a portion of said tip member extends out of said outer flexible member.

4. The apparatus in accordance with claim 3, further comprising: a control member in communication with said flexible fluid carrying member for moving said tip member between said first and second positions.

5. An apparatus for dispensing fluid to an anatomical site from a fluid source while using an endoscope comprising:
   an outer flexible tube;
   a flexible fluid carrying member for receiving fluid from a fluid source, said fluid carrying member disposed at least in part within said outer flexible tube, said flexible member having a distal end and a proximal end;
   a tip member in communication with said distal end of said flexible fluid carrying member;
   said flexible fluid carrying member being coupled to said tip member at said distal end and being coupled to said fluid source at said proximal end;
   said flexible fluid carrying member being movable relative to said outer flexible tube between a first position where said tip member is disposed within said outer flexible tube and a second position where at least a portion of said tip member extends out of said outer flexible tube.

6. The apparatus of claim 5 wherein
   said tip member comprises a hollow needle having a port.

7. The apparatus of claim 5 wherein said tip member comprises a brush.

8. The apparatus of claim 5 wherein
   said tip member includes gauze for permitting fluid flow therethrough for delivery to the anatomical site.

9. The apparatus of claim 5 further comprising:
   a control member in communication with said flexible fluid carrying member for moving said tip member between said first position and said second position.

10. The apparatus of claim 5, further comprising a fluid source in communication with said flexible fluid carrying member.

11. The apparatus of claim 10, wherein said fluid source includes a plunger.

12. The apparatus of claim 11, wherein said plunger includes fluid.

13. The apparatus of claim 12 wherein
   said fluid is selected from the group consisting of anesthetics, steroids, chemotherapeutic agents, antibiotics and mixtures thereof.

* * * * *